(12) United States Patent
Gibes et al.

(10) Patent No.: US 6,380,292 B1
(45) Date of Patent: *Apr. 30, 2002

(54) HYDROPHILIC HOT MELT ADHESIVE

(75) Inventors: Mark Gibes, Port Washington; Diane Strelow, Waukesha; Mark Alper, Mukwonago, all of WI (US)

(73) Assignee: Bostik Findley, Inc., Wauwatosa, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/669,988

(22) Filed: Jun. 21, 1996

(51) Int. Cl.$^7$ ................................. C08L 5/10
(52) U.S. Cl. .................... 524/318; 156/327; 428/317.7; 524/109
(58) Field of Search ...................... 156/327; 428/317.7; 524/318, 109

(56) References Cited

U.S. PATENT DOCUMENTS

| | | | | |
|---|---|---|---|---|
| 2,349,508 A | * | 5/1944 | Mack | ........................ 524/318 |
| 3,419,641 A | * | 12/1968 | Peterkin et al. | ............. 156/327 |
| 3,644,245 A | * | 2/1972 | Flanagan et al. | ............ 156/327 |
| 4,430,468 A | * | 2/1984 | Schumacher | ................ 524/109 |
| 4,434,261 A | * | 2/1984 | Brugel et al. | ................ 156/327 |
| 4,526,577 A | * | 7/1985 | Schmid et al. | .............. 156/327 |
| 4,699,146 A | | 10/1987 | Sieverding | |
| 4,743,238 A | * | 5/1988 | Colon et al. | ................. 524/318 |
| 5,217,798 A | | 6/1993 | Brady et al. | |
| 5,322,876 A | | 6/1994 | Sasaki et al. | |
| 5,356,405 A | | 10/1994 | Thompson et al. | |
| 5,356,963 A | | 10/1994 | Kauffman et al. | |
| 5,685,758 A | | 11/1997 | Paul et al. | ................... 442/409 |

FOREIGN PATENT DOCUMENTS

| | | | |
|---|---|---|---|
| EP | 0634466 | 7/1994 | |
| EP | 0710737 | 10/1995 | |
| EP | 0800833 | 10/1997 | |
| GB | 2294397 | 9/1995 | |
| JP | 60-198251 | * 10/1985 | .............. 428/317.7 |
| WO | WO96/13283 | 9/1995 | |

* cited by examiner

*Primary Examiner*—John J. Gallagher
(74) *Attorney, Agent, or Firm*—Andrus, Sceales, Starke & Sawall, LLP

(57) ABSTRACT

Hydrophilic hot melt adhesive compositions suitable for a variety of applications, especially in nonwoven disposable articles, are prepared by (blending various adhesive components with a surfactant.) The surfactant has a hydrophile-lipophile balance (HLB) number of less than 15, and is incorporated into the composition in an amount such that the resultant adhesive has a contact angle of 75° of less, and preferably less than about 40°. A low contact angle is desirable so that water, urine or other water-based discharges, upon contacting a laminate bound together by the adhesive, wets out rather than beads up resulting in the fluid being directed away from the adhesive and towards an absorbent core of the disposable article.

9 Claims, 5 Drawing Sheets

HYDROPHILIC HOT MELT ADHESIVE

BACKGROUND OF THE INVENTION

The present invention relates to hot melt adhesives, and more specifically to hot melt adhesives having improved hydrophilic properties and which find usefulness in the manufacture of disposable nonwoven articles.

Nonwoven fabric is comprised of an interlocking fiber network, and is employed in the construction of disposable goods. Specific applications of nonwovens have included disposable diapers, sanitary napkins, surgical drapes, hospital pads and adult incontinence products.

In such applications it is generally necessary to adhere nonwoven, tissue, absorbent fluff or the like to another substrate. This second substrate may be another nonwoven fabric, tissue, or a material such as a polyolefin e.g. a polyethylene or polypropylene layer. Typically, a hot melt adhesive has been used to bond such materials together since there is no evaporation step necessary during manufacture, as would be the case for water-based or solvent-based adhesives. Suitable hot melt adhesives must possess the appropriate bond strength to adhere the substrates involved, and must also possess good flexibility, no staining or bleed through, suitable viscosity and open time to function on commercial equipment, acceptable stability under storage conditions, and acceptable thermal stability under normal application conditions.

Many different polymers have been used in hot melt adhesives employed in the construction of disposable nonwoven goods. In this regard typical hot melt adhesives have employed polymers which have included S-I-S (styrene-isoprene-styrene); SBS (styrene-butadiene-styrene); SEBS (styrene-ethylene-butylene-styrene); EVA (ethylene vinyl acetate); and APAO (amorphous poly alpha olefin). While these polymers, when properly blended, provide acceptable adhesion between most substrates employed in typical nonwoven construction such as diapers, and further provide acceptable adhesion under dry conditions, they have had several shortcomings which have detracted from their usefulness.

One of the most noteworthy shortcomings of prior hot melt adhesives concerns the manner in which the adhesive, which is typically very hydrophobic, reacts when exposed to liquids, such as water, urine, or the like. Normally, one would expect the hydrophobic character of hot melt adhesives to be an advantage since such adhesives will provide good dry bonds and will normally maintain an acceptable bond strength when wet. However, manufacturers of disposable nonwoven articles such as diapers have endeavored to produce products which are much thinner in their overall thickness and profile and which incorporate super absorbent materials in place of fluff, which is normally in the core. Thus, it is extremely important in such nonwoven constructions to insure that water, urine or other water-based discharges or solutions are directed toward the absorbent core as quickly as possible, and that any material that might hinder such action be eliminated or at least minimized. As a result, one can now readily understand why the hydrophobicity of typical hot melt adhesives is undesirable since it is a characteristic which inherently hinders fluid transfer into the core of such articles.

Therefore, it has long been known that it would be desirable to have a hot melt adhesive which is useful for bonding to substrates which are typically employed in the construction of nonwoven articles, such as polyethylene, polypropylene, nonwoven, tissue, or fluff, and which further maintains acceptable wet bond strength following exposure for prolonged periods of time to water, urine or similar materials. At the same time, such adhesives should be more hydrophilic to not hinder fluid transfer into the absorbent core of such articles.

SUMMARY OF THE INVENTION

It is therefore an object of the present invention to provide an improved hot melt adhesive which is useful for the manufacture of disposable nonwoven articles.

A further object of the present invention is to provide a hot melt adhesive which can be employed as a construction adhesive, and which further will be sufficiently hydrophilic to aid in fluid transfer into the absorbent core of disposable nonwoven articles.

In order to accomplish the above objects, the present invention provides a hot melt adhesive having the following composition (by weight):

about 10–50% of a polymer;
about 40–80% of a tackifying resin;
about 0–40% of a plasticizer;
about 0.1–2% of an antioxidant; and
about 0.1–30% of a surfactant, the components totaling 100% by weight. The surfactant has a hydrophilic-lipophilic balance (HLB) number of less than 15, and is incorporated into the composition in an amount such that the resultant adhesive has a contact angle of 75° or less, and preferably less than about 40°. A low contact angle is desirable so that water, urine or other water-based discharges "wet out" rather than "bead up" resulting in the fluid being directed away from the adhesive.

It will also decrease the chance of fluid leakage from such articles and help improve the absorption in thinner superabsorbent filled articles by directing the fluid more quickly toward the core. This is accomplished by applying the hydrophilic hot melt adhesive of the present invention to one substrate of a disposable nonwoven absorbent article in a configuration such that fluid is directed toward or "wicked" toward a desired absorbent location in one of the substrates. For example, if the disposable article is a diaper, the adhesive might be applied in a rectangular pattern centrally in the crotch region of a nonwoven substrate. This would result in urine being directed toward the crotch region of the absorbent core, rather than the leg cuff region or waist region of the diaper.

The adhesives of the instant invention are especially suited for use in absorbent products such as diapers, training pants, incontinent products, feminine care products, and medical products. With all of these products there is a need to bond the layers or substrates of the article together and hot melts are often used as discussed above. Usually the core area of the article is adhered by spraying a layer of adhesive onto a nonwoven substrate and adhering it to an absorbent core. In many cases, a layer of tissue is placed between the nonwoven and the core, sometimes fully wrapping the core and in other cases simply covering the top layer. Another layer of adhesive may be used to bond the absorbent core fluff to the tissue and further another layer of adhesive may bond the tissue or fluff to the backsheet (which is often polyethylene or a composite laminate). So there is at least one and often a number of layers of sprayed hot melt used in bonding the core into place. If the nonwoven topsheet and core are not in good contact, "tenting" of the nonwoven can occur, which can dramatically decrease absorption.

The adhesive further holds the core in place and can help to prevent core cracking. Core cracking can prevent the proper flow of liquids within the core itself and cause leakage. To improve resistance to wet debonding and core cracking, a distinct class of hot melts has been developed having high wet bond strength which represent an improvement over conventional adhesives since they retain the bond to both the tissue and the core when wet.

Unfortunately, the process of placing layers of sprayed hot melt in the area of the core can actually decrease the fluid uptake, since the adhesive itself is quite hydrophobic. Although the new class of high wet bond strength adhesives mentioned above are resistant to debonding under wet conditions, they have also been hydrophobic. The adhesives of the instant invention are very hydrophilic and eliminate this shortcoming, even improving the fluid acquisition of the core over no adhesive (see Examples 2–3). They also can be formulated to be hydrophilic and also have improved the resistance to debonding under wet conditions, like the new class of adhesives mentioned above (see Example 4).

These adhesives show obvious utility in the core area bonding each of the layers in a particular absorbent article together without inhibiting the absorbency of the structure. Absorbent cores can be found in articles such as diapers, incontinent products, feminine care products, medical devices and the like. Often superabsorbents (SAP) as used in absorbent articles to improve the rate and holding power of the cellulosic absorbent material in the core. These SAPs are sometimes bonded into place with hot melts. As can be readily appreciated, these hot melts can slow down the rate of absorbency of the SAP due to their hydrophobic nature. The hydrophilic adhesives of this invention could also be used in this application.

The top layer of absorbent articles needs to allow fluids to readily pass through it. This layer is often a nonwoven or some type of fabric based on polymers such as polyethylene or polypropylene. While these fabrics and apperturned films work well as coverstocks, it will be recognized that they are by nature hydrophobic. A bead of liquid placed on these materials will not easily pass through even though the fabric has many open pores. To get around this obvious problem, manufacturers of these materials have had to treat the materials to make them more hydrophilic (often by a surface treatment). In other cases, the manufacturers of absorbent articles have sprayed surfactants or other materials onto the materials during processing. Spraying these materials causes problems in housekeeping of the manufacturing line and the atomized materials can fill the air and be an irritant to operators. These materials also have no use other than to make the topsheet hydrophilic. Also, these surfactants can migrate to other parts of the article and cause the hot melts to debond. It will be noted that the adhesives of this invention could be used both to bond the article together and also to allow use of standard hydrophobic topsheets. The hydrophilic character could be carried to the article to selectively treat areas, allowing greater freedom of absorbent article design.

There are other applications where it is desirable to make a material breathable, that is, to allow moisture (such as sweat) to flow through a laminate. This may be useful both in articles such as diapers and in medical articles. This invention could also be used to improve flow over typical hydrophobic hot melts in such applications.

DETAILED DESCRIPTION OF THE PREFERRED EMBODIMENT

Figure 1:
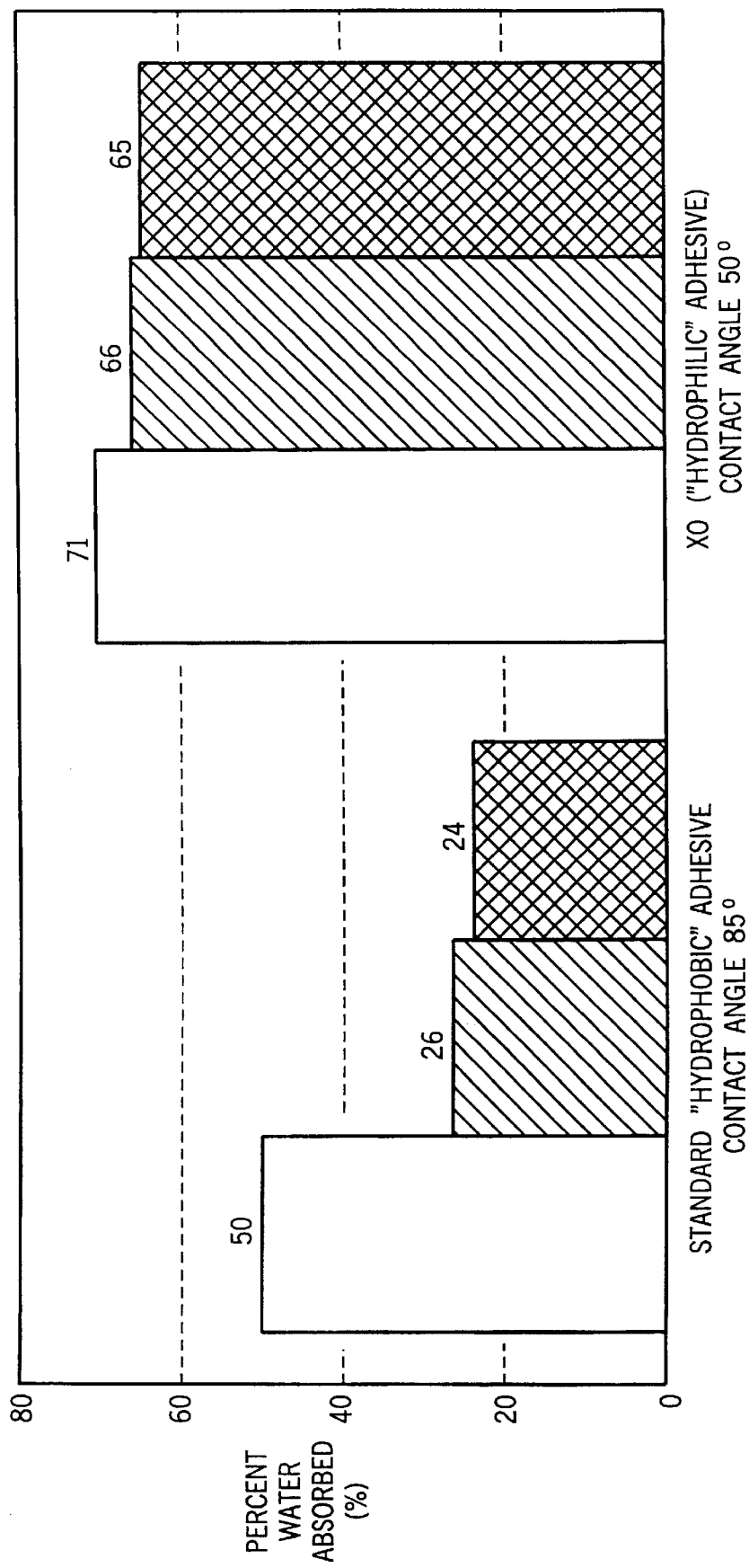
FIG. 1 is a bar graph comparing the percent water which passed through a nonwoven to tissue laminate that was absorbed by a towel wherein the laminate was bonded together with a typical prior art hydrophobic hot melt adhesive having a contact angle of 85° in one test versus a hydrophilic hot melt adhesive formulated in accordance with the present invention in a second test.

A hydrophilic hot melt adhesive composition having ingredients in the following ranges provides advantages over current technology when evaluated for wettability. More particularly, the adhesive composition of the present invention has the following ingredients by weight;

about 10–50% of a polymer;

about 40–80% of a tackifying resin;

about 0–40% of a plasticizer;

about 0.1–2% of an antioxidant; and about 0.1–30% of a surfactant, the components totaling 100% by weight.

Any of a variety of available thermoplastic materials can be used as the polymer in the compositions of the invention in an amount from about 10% to about 50% by weight, preferably from about 15% to about 25%. Examples of such materials include ethylene based polymers, including ethylene/vinyl acetate, ethylene acrylate, ethylene methacrylate, ethylene methyl acrylate, ethylene methyl methacrylate, polybutylene, high and low density polyethylene, polyethylene blends and chemically modified polyethylene, copolymers of ethylene and 1–6 mono- or di-unsaturated monomers, polyamides, polybutadiene rubber, polyesters such as polyethylene terephthalate, polybutylene terephthalate; thermoplastic polycarbonates, atactic poly-alphaolefins, including atactic polyproylene, and others; thermoplastic polyacrylamides, polyacrylonitrile, copolymers of acrylonitrile and other monomers such as butadiene styrene; polymethyl pentene, polyphenylene sulfide, aromatic polyurethanes; styrene-acrylonitrile, acrylonitrile-butadiene-styrene, styrene-butadiene rubbers, polyethylene terephthalate, acrylonitrile-butadiene-styrene elastomers, polyphenylene sulfide, A-B, A-B-A, A-(B-A)$_n$-B, (A-B)$_n$-Y block polymers wherein the A comprises a polyvinyl aromatic block, the B block comprises a rubbery midblock which can be partly hydrogenated, and mixtures of said substances.

Preferred polymers for use in the adhesives of this invention comprise EVA, APP, polybutylene, linear A-B-A block, linear A-(B-A)$_n$-B multiblock copolymers, and radial or teleblock copolymers of the formula (A-B)$_n$-Y wherein A comprises a polystyrene block, B comprises a substantially rubbery polybutadiene or polyisoprene block, Y comprises a multivalent compound, and n is an integer of at least 3. The midblocks can be post-treated to improve their heat stability through hydrogenation or other post-treatment removing residual unsaturation. The size and the amount of the A or end blocks in the A-B-A block copolymer structure may be as much as 15–51 wt-% of the polymer.

While the total styrene content of the polymers can be as much as 51 wt-% of the polymer, and since the polymers can have more than two A blocks for optimal performance, the total A block should be less than or equal to about 45 wt-% of the polymers, and, most preferably, is less than or equal to 35 wt-% of the polymer. In an S-B-S (styrene-butadiene-styrene) copolymer, the preferred molecular weight is about 50,000 to 120,000, and the preferred styrene content is about 20 to 45 wt-%. In an S-I-S (styrene-isoprene-styrene) copolymer, the preferred molecular weight is about 100,000 to 200,000 and the preferred styrene content is about 14–35 wt-%. Hydrogenating the butadiene midblocks produces rubbery midblocks that are typically considered to ethylene-butylene midblocks.

Such block copolymers are available from Shell Chemical Company, Enichem, Fina and Dexco. Multiblock or tapered block copolymers (the A-(B-A)$_n$-B type) are available from Firestone.

The tackifying resins which are used in the hot melt construction adhesives of the present invention are those which extend the adhesive properties and improve the specific adhesion of the polymer. As used herein, the term "tackifying resin" includes:

(a) natural and modified rosin such as, for example, gum rosin, wood rosin, tall-oil rosin, distilled rosin, hydrogenated rosin, dimerized rosin and polymerized rosin;

(b) glycerol and pentaerythritol esters of natural and modified rosins, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall oil rosin and the phenolic modified pentaerythritol ester of rosin;

(c) polyterpene resins having a softening point, as determined by ASTM method E28-58T, of from about 60° C. to 140° C., the latter polyterpene resins generally resulting from the polymerization of terpene hydrocarbons, such as the monoterpene known as pinene, in the presence of Friedel-Crafts catalysts at moderately low temperatures; also included are the hydrogenated polyterpene resins;

(d) copolymers and terpolymers of natural terpenes, e.g. styrene/terpene, α-methyl styrene/terpene and vinyl toluene/terpene;

(e) phenolic-modified terpene resins such as, for example, the resin product resulting from the condensation, in an acidic medium, of a terpene and a phenol;

(f) aliphatic petroleum hydrocarbon resins having Ring and Ball softening points of from about 60° to 140° C., the latter resins resulting from the polymerization of monomers consisting primarily of olefins and diolefins; also included are the hydrogenated aliphatic petroleum hydrocarbon resins; examples of such commercially available resins based on a $C_5$-olefin fraction of this type are "Wingtack 95" and "Wingtack 115" tackifying resins sold by Goodyear Tire and Rubber Company;

(g) aromatic petroleum hydrocarbons and the hydrogenated derivatives thereof;

(h) aliphatic/aromatic petroleum derived hydrocarbons and the hydrogenated derivatives thereof.

Mixtures of two or more of the above described tackifying resins may be required for some formulations. Although a range of 40–80% by weight tackifying resin may be used, the preferred range is 50% to 65%. An example of a commercially available tackifying resin which is useful for the present invention includes the resin which is identified commercially by the trade designation Unitac R100L. This resin is a pentaerythritol based tall-oil rosin ester, and is available from Union Camp.

A plasticizer can be present in the composition of the present invention in amounts of about 0% to about 40% by weight, preferably from about 10% to about 30%, in order to provide desired viscosity control without substantially decreasing the adhesive strength or the service temperature of the adhesive. A suitable plasticizer may be selected from the group which not only includes the usual plasticizing oils, such as mineral oil, but also olefin oligomers and low molecular weight polymers, as well as vegetable and animal oil and derivatives of such oils. The petroleum derived oils which may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 350 and about 10,000. Suitable vegetable and animals oils include glycerol esters of the usual fatty acids and polymerization products thereof. The plasticizer that finds usefulness in the present invention can be any number of different plasticizers but the inventors have discovered that mineral oil such as Kaydol manufactured by Witco, is particularly useful in the present invention. Benzoflex 9–88, a dipropylene glycol dibenzoate manufactured by Velsicol, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications).

Waxes in the composition of the present invention are used to reduce the melt viscosity of the hot melt construction adhesives without appreciably decreasing their adhesive bonding characteristics. These waxes also are used to reduce the open time of the composition without effecting the temperature performance. Among the useful waxes are:

(1) low molecular weight, that is, 1000–6000, polyethylene having a hardness value, as determined by ASTM method D-1321, of from about 0.1 to 120 and ASTM softening points of from about 150° to 250° F.:

(2) petroleum waxes such as paraffin wax having a melting point of from about 130° to 170° F. and microcrystalline wax having a melting point of from about 135° to 200° F., the latter melting points being determined by ASTM method D127-60;

(3) atactic polypropylene having a Ring and Ball softening point of from about 120° to 160° C.;

(4) synthetic waxes made by polymerizing carbon monoxide and hydrogen such as Fischer-Tropsch wax; and (5) polyolefin waxes. As used herein, the term "polyolefin wax" refers to those polymeric or long-chain entities comprised of olefinic monomer units. These materials are commercially available from Eastman Chemical Co. under the trade name "Epolene." The materials which are preferred to use in the compositions of the present invention have a Ring and Ball softening point of 200° F. to 350° F. As should be understood, each of these wax diluents is solid at room temperature. Other useful substances include hydrogenated animal, fish and vegetable fats and oils such as hydrogenated tallow, lard, soya oil, cottonseed oil, castor oil, menhadin oil, cod liver oil, etc., and which are solid at ambient temperature by virtue of their being hydrogenated, have also been found to be useful with respect to functioning as a wax diluent equivalent. These hydrogenated materials are often referred to in the adhesives industry as "animal or vegetable waxes." Additionally, hydrocarbon oils, especially naphthenic or paraffinic process oils, may also be employed herein as the wax diluent.

The present invention includes a stabilizer or antioxidant in an amount of from about 0.1% to about 2% by weight, but preferably from about 0.1% to 1%. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by a deterioration in the appearance, physical properties and performance characteristics of the adhesive. A particularly preferred antioxidant in Irganox 1010, a tetrakis(methylene(3,5-di-teri-butyl-4-hydroxyhydrocinnamate))methane manufactured by Ciba-Geigy. Among the applicable stabilizers are high molecular weight hindered phenols and multifunctional phenols, such as sulfur and phosphorus-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3-5-di-tert-butyl-4-hydroxybenzyl)benzene;

pentaerythritol tetrakis-3(3,5-di-tert-butyl-4-hydroxyphenyl)propionate;

n-octadecyl-3(3,5-ditert-butyl-4-hydroxyphenyl) propionate;

4,4'-methylenebis(4-methyl-6-tert butylphenol);

4,4'-thiobis (6-tert-butyl-o-cresol);

2,6-di-tert-butylphenol;

6-(4-hydroxyphenoxy)-2,4-bis(n-ocytlthio)-1,3,5-triazine;

2,4,6-tris(4-hydroxy-3,5-di-tert-butyl-phenoxy)-1,3,5-triazine;

di-n-octadecyl-3,5-di-tert-butyl-4-hydroxybenzylphosphonate;

2-(n-octylthio)ethyl-3,5-di-tert-butyl-4-hydroxybenzoate; and sorbitol hexa-(3,3,5-di-tert-butyl-4-hydroxy-phenyl) propionate.

Especially preferred as a stabilizer is pentaerythritol tetrakis-3(3,5-di-tert-butyl-4-hydroxyphenol)propionate.

The performance of these stabilizers may be further enhanced by utilizing, in conjunction therewith; (1) synergists such as, for example, as thiodipropionate esters and phosphates; and (2) chelating agents and metal deactivators as, for example, ethylenediaminetetraacetic acid, salts thereof, and disalicylalpropylenediimine.

The hot melt adhesive composition of the present invention may be formulated using any of the techniques known in the art. A representative example of the prior art procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of about 250° F. to 350° F. It should be understood that the precise temperature to be used in this step would depend on the melting point of the particular ingredients. The resulting adhesive composition is agitated until the polymers completely dissolve. A vacuum is then applied to remove any entrapped air.

Optional additives may be incorporated into the hot melt constructions adhesive composition in order to modify particular physical properties. These additives may include colorants, such as titanium dioxide.

The surfactant can be present in the composition of the present invention in amounts of from about 0.1% to about 30%, by weight, and preferably from about 1% to about 10% in order to make the adhesive more hydrophilic. The surfactant has a hydrophile-lipophile balance (HLB) number of less than 15, and is incorporated into the composition in an amount such that the resultant adhesive has a contact angle of 75° or less, and preferably less than about 40°. A low contact angle is desirable so that water, urine or other water-based discharges "wet out" rather than "bead up" resulting in the fluid being directed away from the adhesive.

The HLB of a surfactant is an expression of its hydrophile-lipophile balance, i.e. the balance of the size and strength of the hydrophilic (water-loving or polar) and the lipophilic (oil-loving or non-polar) groups of the surfactant. All surfactants consist of a molecule that combines both hydrophilic and lipophilic groups.

The surfactant must be reasonably compatible with the other raw materials used in the hot melt adhesive so that it does not adversely affect the construction performance of the adhesive. On the other hand, the surfactant must "bloom" to the surface of the adhesive so as to lower the contact angle and make the adhesive more hydrophilic. Thus, a delicate balance of compatibility must be maintained. The surfactant also should not contain any water or other solvents making it processable in hot melt mixing equipment and non-toxic for the end user. The surfactant also must be sufficiently stable and non-volatile to allow processing in hot melt manufacturing and application equipment without effect on the adhesive.

As used herein, the term "surfactant" or "surface-active agent" refers to any compound that reduces surface tension when dissolved in water or water solutions, or which reduces interfacial tension between two liquids, or between a liquid and a solid. Examples of suitable surfactants include, but are not limited to, the following:

(1) Fatty acid esters such as glycerol esters, PEG esters, and sorbitan esters, including ethylene glycol distearate, ethylene glycol monostrearate, glycerol mono and/or dioleate, PEG dioleate, PEG monolaurate, sorbitan monolaurate, sorbitan trioleate, etc. These surfactants are available from ICI, Rhone-Poulenc, and other sources.

(2) Nonionic ethoxylates,such as alkylphenol ethoxylates, alcohol ethoxylates, alkylamine ethoxylates, etc., including octylphenol ethoxylate, nonylphenol ethoxylate, alkylamine ethoxylates, etc. These surfactants are available from Rhone-Poulenc, Union Carbide, and other sources.

(3) Nonionic surfactants such as 2,4,7,9-tetramethyl-5-decyn-4,7-diol available from Air Products.

(4) Ethylene oxide/Propylene oxide copolymers, which are available from Union Carbide, BASF, etc. It should be noted that these and other surfactants can be blended if necessary to produce the best blend of hydrophilic performance properties.

Atmer 688, a nonionic surfactant blend, and Alkamuls GMS/C a glycerol monostearate, both manufactured by ICI Americas Inc. have been found to be preferred surfactants for use in the present adhesive composition.

Contact angle measurements of liquid droplets on substrate surfaces are used to characterize surface wettability. The lower the contact angle, the more hydrophilic is the adhesive. The contact angle is defined as the angle between the substrate support surface and the tangent line at the point of contact of the liquid droplet with the substrate. The value of the contact angle of the liquid droplet will depend upon the surface energy of the substrate and the surface tension of the liquid. If complete wetting takes place between the liquid and the substrate surface, the droplet will spread out over the substrate and the contact angle will approach zero, whereas if wetting is only partial, the resulting contact angle will lie in the range of 0 to 180 degrees. The contact angles reported in FIGS. 1 and 2, as well as those in Table 1, were all performed with a model CAM-FILM contact angle meter available from Tantec Inc. using the half-angle measuring method described in U.S. Pat. No. 5,268,733.

Referring now to FIG. 1, there is illustrated a bar graph comparing the percent water absorbed through a laminate into a towel which was covered by the laminate. The laminate was a nonwoven substrate bonded to a tissue layer. The bond was formed with a prior art hydrophobic hot melt adhesive having a contact angle of 85°, or a hydrophilic hot melt adhesive (XO) having a contact angle of 50° formulated in accordance with the present invention. Each adhesive was tested at three different add-on levels, i.e. 1 mg/in$^2$, 3 mg/in$^2$ and 10 mg/in$^2$. The test was performed by placing a towel on a flat support, covering the towel with the laminate, and then raising one edge of the support so that the towel and laminate are elevated at a 30° angle. 3 grams of water were then poured onto the laminate. The weight of the wet towel was then taken and compared to its original dry weight to determine the percent water absorbed.

As illustrated, the hydrophilic adhesive of the present invention is clearly superior to the prior art hydrophobic adhesive in wettability. The percent water absorbed by the towel ranged from 65%–71% using the present hydrophilic adhesive (XO) whereas absorption was only 25%–50% using the prior art hydrophobic adhesive. Thus, the hydrophilic adhesive (XO) permitted significantly greater fluid absorption by the towel.

Figure 2:
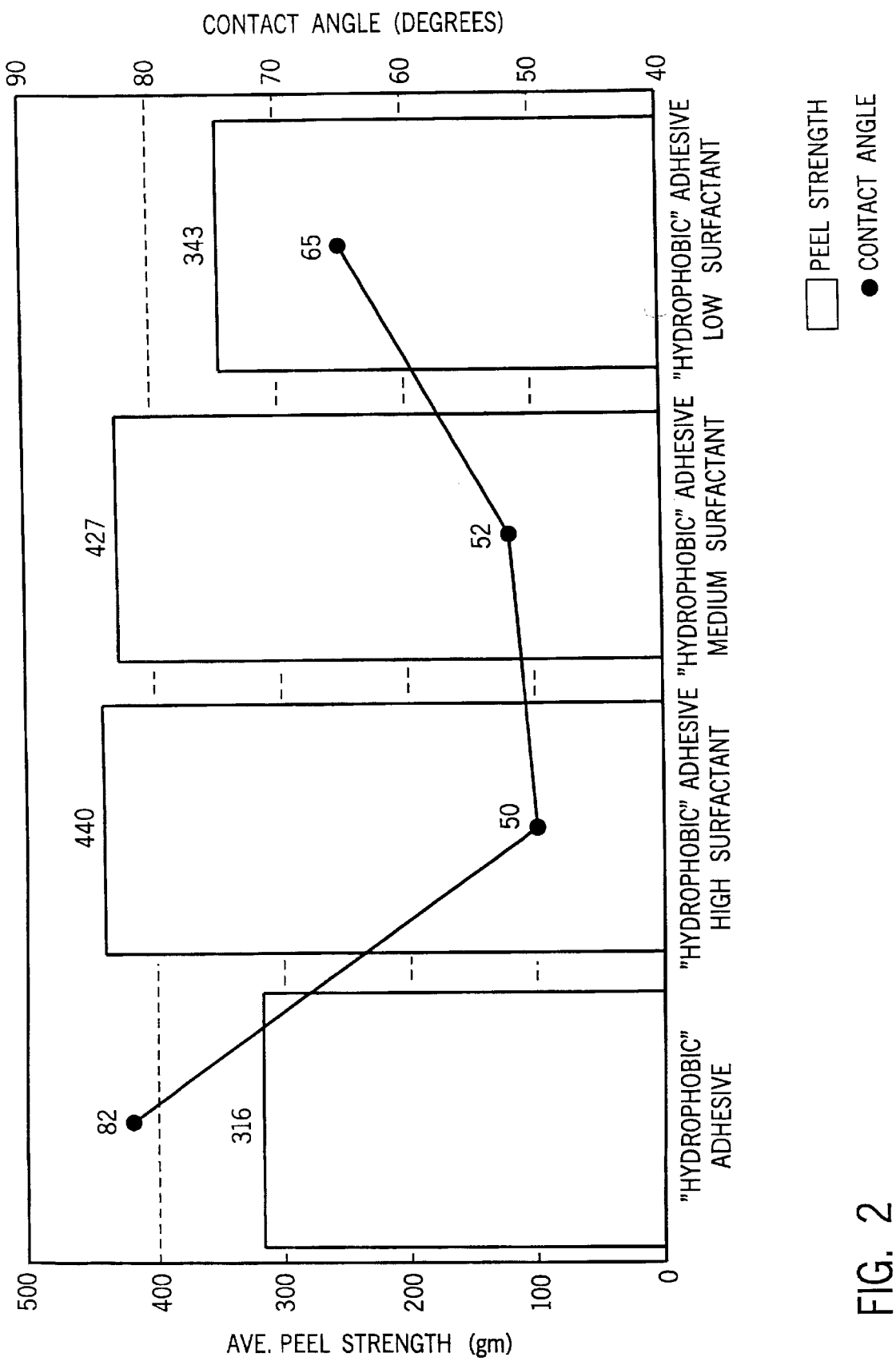
FIG. 2 is a bar graph comparing the average peel strength and contact angle for various hot melt adhesives.

FIG. 2 illustrates a bar graph comparing average peel strength and contact angles for various hot melt adhesives. FIG. 2 demonstrates that hydrophilic adhesives made in accordance with the present invention, all of which have a contact angle of less than 75°, retain sufficient peel strength to be used as a construction adhesive in nonwoven articles such as diapers. In these tests, laminates were formed using polyethylene (PE) and nonwoven (NW) substrates bonded together with the designated adhesive having an add-on of 3 mg/in$^2$. The contact angle was determined for each different adhesive and plotted as shown by the solid line. The samples were tested for Instron peel strength at a cross head speed of 12 inches/minute, and is the average of five tests. Also, it should be noted that the term "high" in FIG. 2 refers to the amount of surfactant added to the adhesive, which was 15%. The term "medium" refers to the addition of 10% surfactant to the adhesive formulation while "low" refers to the use of 5% surfactant in the formulation.

Figure 3:
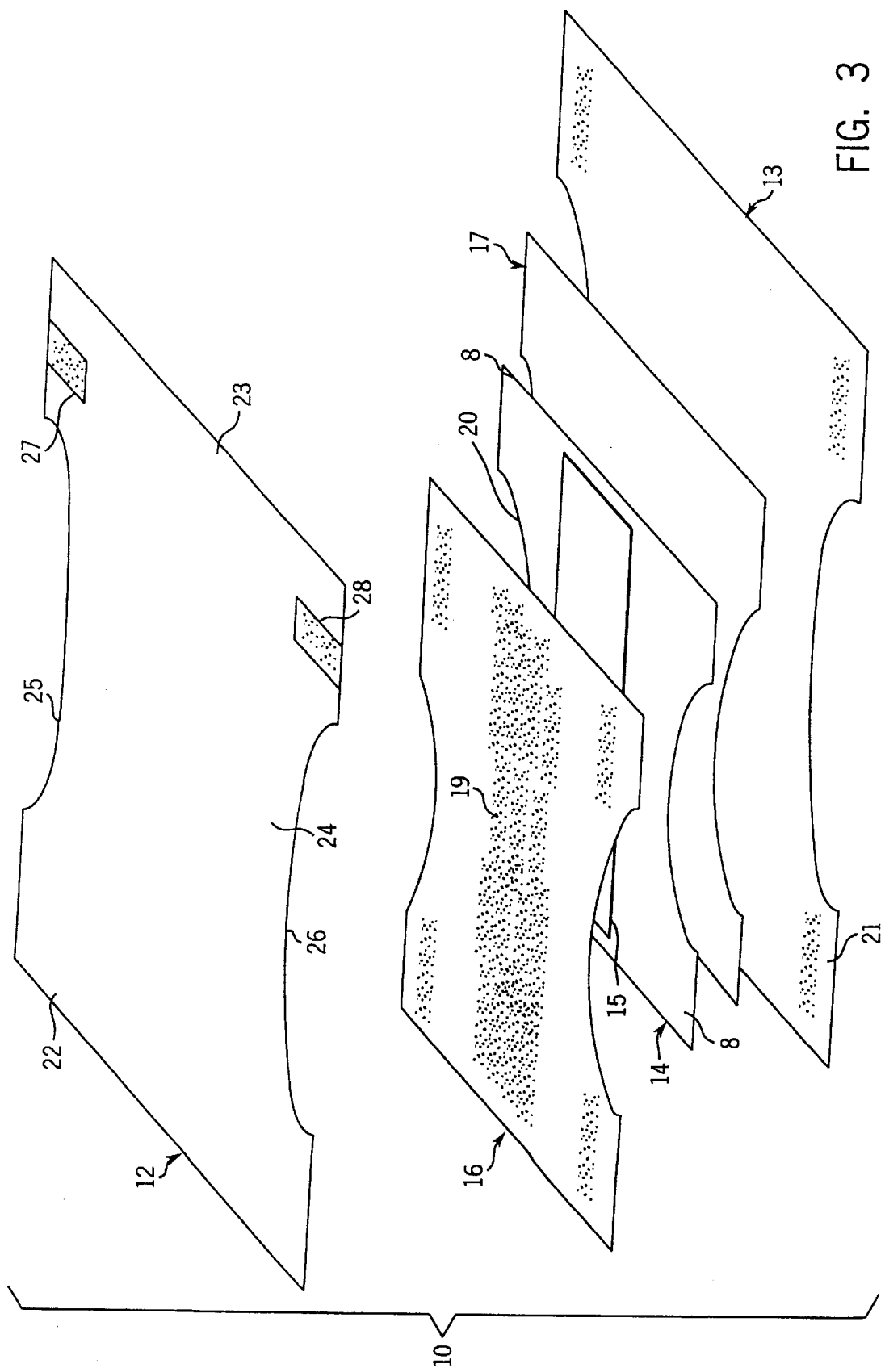
FIG. 3 is a schematic, exploded, perspective view of a disposable diaper incorporating a hydrophilic hot melt adhesive of the present invention.
Figure 4:
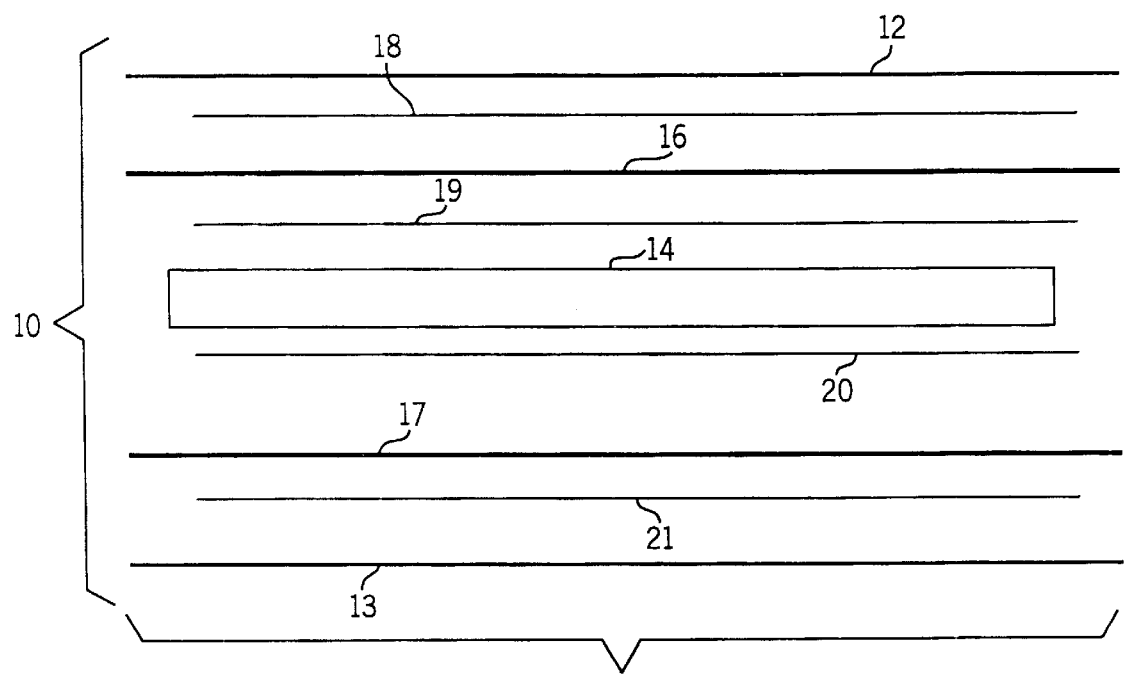
FIG. 4 is a schematic cross sectional view of the diaper of FIG. 3.

Referring now to FIGS. 3 and 4, there is illustrated in FIG. 3 an exploded view of various substrates comprising a diaper 10 in its flat, uncontracted state with portions of the structure being shown schematically to more clearly show the construction of diaper 10. FIG. 4 schematically illustrates in cross section the multiple layers or substrates of the diaper 10. As used herein, the term "diaper" refers to an absorbent article typically worn by infants, young children and incontinent persons. As readily understood, such an absorbent article is worn about the lower torso of the wearer and is held in place about the wearer's hips. It should be understood, however, that the present invention is also applicable to other absorbent articles such as training pants, incontinent products such as briefs and undergarments, feminine care products such as sanitary napkins and pantyliners, medical products, such as surgical drapes, and the like.

As used herein, the term "absorbent article" refers to a device or product which absorbs and contains body fluids and exudates such as urine. More specifically, this term refers to such devices or articles that are worn against or in proximity to the body of a wearer to absorb and contain various fluids and exudates discharged from the body. The term "disposable" is used herein to describe absorbent articles which are to be discarded after a single use. Such articles are not intended to be laundered or otherwise re-used as an absorbent article. Preferred embodiments of absorbent articles of the present invention are the diaper 10 schematically shown in FIG. 3 and the feminine care pad 11 schematically illustrated in FIG. 5.

As shown in FIGS. 3 and 4, diaper 10 comprises multiple layers of sheet material or substrates bonded together to form the absorbent article. More specifically, diaper 10 includes a fluid pervious nonwoven topsheet 12 and a fluid impervious backsheet 13 (typically made of polyethylene) joined with topsheet 12. An absorbent core 14 is positioned between topsheet 12 and backsheet 13. Absorbent core 14 may be comprised of fluff 8 and a centrally disposed superabsorbent (SAP) material 15. Diaper 10 may also include a top tissue layer 16 disposed between topsheet 12 and core 14 as well as a bottom tissue layer 17 disposed between backsheet 13 and core 14. As shown best in FIG. 4, each substrate is bonded to an adjacent substrate by a layer of adhesive formulated in accordance with the present invention. For example, nonwoven topsheet 12 is bonded to top tissue layer 16 by a layer of adhesive 18 applied to the underside of topsheet 12. In turn, top tissue layer 16 is bonded to core 14 by a layer of adhesive 19. Core 14 is bonded to bottom tissue layer 17 by a layer of adhesive 20 and bottom tissue layer 17 in turn is bonded to backsheet 13 by a layer of adhesive 21 applied to the upper surface of backsheet 13. The adhesive may be spiral sprayed, melt blown, slot applied or may be applied as a bead depending upon the location and the type of bond desired.

As shown best in FIG. 3, diaper 10 includes a pair of opposite waist panels 22, 23 interconnecting a crotch portion 24. Crotch portion 24 in turn includes a pair of opposite elasticized leg cuffs 25, 26. The waist panels 22, 23 are held together when diaper 10 is worn by a user by a fastening system which is illustrated in FIG. 3 as a pair of releasable tape tabs 27, 28.

Figure 5:
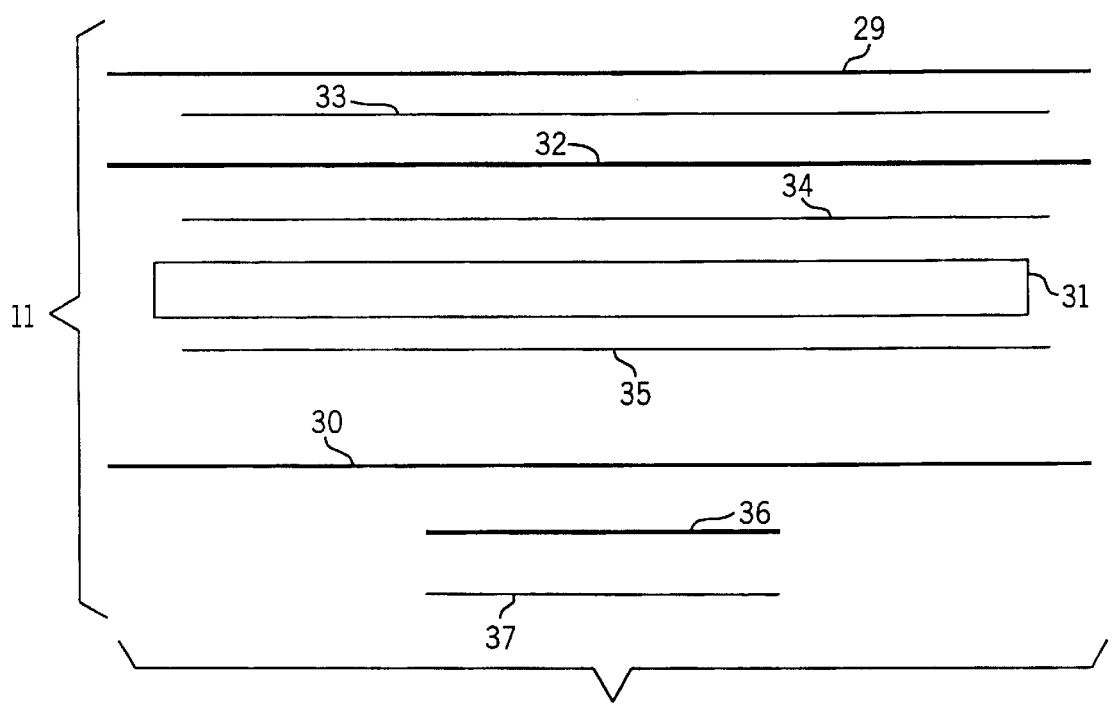
FIG. 5 is a schematic cross sectional view of a disposable feminine care pad incorporating a hydrophilic hot melt adhesive of the present invention.

Referring now to FIG. 5, there is illustrated an absorbent article illustrating a typical feminine care pad 11. Pad 11 comprises multiple layers of sheet material or substrates bonded together to form the absorbent article. More particularly, pad 11 includes a fluid pervious nonwoven topsheet 29 and a fluid impervious backsheet 30 (typically made of polyethylene) joined with topsheet 29. An absorbent core 31 is positioned between topsheet 29 and backsheet 30. Absorbent core 31 may be comprised of fluff and/or super absorbent (SAP) material. Pad 11 may also include a top tissue layer 32 disposed between topsheet 29 and core 31. As shown in FIG. 5, each substrate is bonded to an adjacent substrate by a layer of adhesive formulated in accordance with the present invention. For example, nonwoven topsheet 29 is bonded to top tissue layer 32 by a layer of adhesive 33 applied to the underside of topsheet 29. In turn, top tissue layer 32 is bonded to core 31 by a layer of adhesive 34. Finally, core 31 is bonded to backsheet 30 by a layer of adhesive 35 applied to the upper surface of backsheet 30. In the embodiment illustrated in FIG. 5, there is also a layer of adhesive 36 applied to the bottom side of backsheet 30 and release paper 37 covering adhesive 36. Thus, when paper 37 is removed to expose adhesive 36, adhesive layer 36 may be utilized to attach pad 11 to an undergarment worn by the user, as is conventional and well-known in the art.

Figure 6:
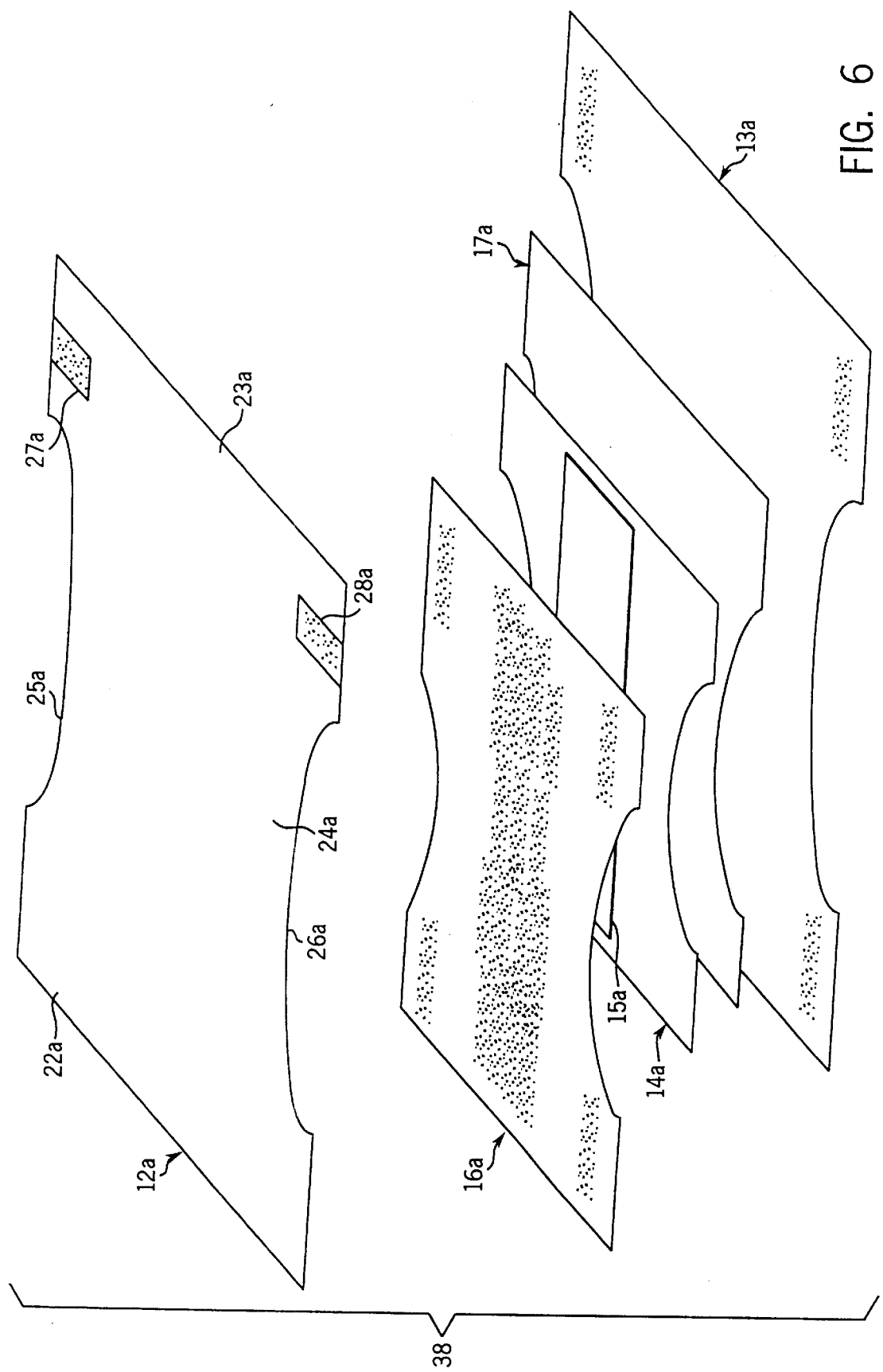
FIG. 6 is a schematic, exploded perspective view of a disposable diaper similar to FIG. 1 incorporating a hydrophilic hot melt adhesive of the present invention applied to its nonwoven top sheet in such a manner so as to provide wicking of fluids toward the center of the diaper.

Referring now to FIG. 6, there is illustrated a diaper 38 similar to diaper 10 shown in FIGS. 3 and 4. Accordingly, like numbers are employed in FIG. 6 for like components except with the designation of "a" thereafter. Diaper 38, however, incorporates a hydrophilic hot melt adhesive formulated in accordance with the present invention and applied to its nonwoven topsheet 12a in such a manner so as to provide wicking of fluids toward the center of diaper 38. In order to accomplish this, FIG. 6 illustrates a rectangular configuration 39 of adhesive applied to the underside of topsheet 12a in the crotch portion 24a. Application of the adhesive in this portion of diaper 38 selectively improves fluid penetration in crotch portion 24a over other sections such as waste panels 22a, 23a and leg cuffs 25a, 26a of top sheet 12a. This is due to the hydrophilic characteristic of the adhesive in configuration 39. Although shown in a rectangular configuration, other configurations could potentially be employed, such as oval shapes, football shapes, figure 8 shapes, circular shapes, and the like, all of which would be employed to direct fluid toward a desired absorbent location in one of the substrates of an absorbent article such as a diaper or care pad.

The invention is further illustrated by way of the examples which are set forth below.

EXAMPLES 1–5

The following adhesive blends were prepared in accordance with the percentages shown in Table 1. Example 1 is a typical prior art hydrophobic adhesive without any surfactant added. Examples 2–4 were all formulated using varying amounts of surfactant in accordance with the present invention. When tested, the formulations of Examples 2–4 all demonstrated sufficient peel strength to function as a construction adhesive while also providing a low contact angle resulting in sufficient hydrophilic characteristics to provide wettability.

TABLE 1

| Components | Example 1 | Example 2 | Example 3 | Example 4 |
|---|---|---|---|---|
| Unitac R100L | 57.5 | 57.5 | 57.5 | 57.5 |
| Stereon 840A (SBS) | 20 | 20 | 20 | |
| SolT 193B (SIS) | | | | 22.5 |
| Kaydol | 22.5 | 17.5 | 15 | |
| Benzoflex 9-88 | | | | 12.5 |
| Atmer 688 | | 5 | 7.5 | 5 |
| Alkamuls GMS/C | | | | 2.5 |
| Irganox 1010 | 1 | 1 | 1 | 1 |
| Viscosity @ 325° F. (cP) | 1235 | 1320 | 1295 | 1730 |
| Ring & Ball Softening point (° F.) | 155 | 150 | 146 | 163 |
| Contact Angle (°) | 88 | 32 | 16 | 16 |
| Ave. Peel Strength (gm) | 87 | 85 | 86 | 91 |

Raw Materials

| | |
|---|---|
| Unitac R100L | 100° C. mp, PE tall-oil rosin ester, Union Camp |
| Stereon 840A | SBS block copolymer, Firestone |
| SolT193B | SIS block copolymer; Enichem |
| Kaydol | mineral oil, Witco |
| Benzoflex 9-88 | dipropylene glycol dibenzoate, Velsicol |
| Atmer 688 | nonionic surfactant blend, ICI |
| Alkamuls GMS/C | glycerol monostrearate, Rhone-Poulenc |
| Irganox 1010 | tetrakis(methylene(3,5-di-tert-butyl-4-hydroxyhydrocinnamate))methane Ciba-Geigy |
| Coating Conditions: | PE to NW laminates, 3.0 mg/in$^2$ Spiral Spray, 0.5 sec. open time, 325° F. Adhesive, 400° F. Air. |
| Instron Peel Strength: | Average peel strength at 12 inches/minute |

We claim:

1. A hydrophilic hot melt adhesive composition, comprising the following components:

about 10–50% of a thermoplastic polymer selected from the group consisting of polybutylenes, S-I-S and S-B-S styrenic block copolymers, and atactic polyalphaolefins;

about 40–80% of a tackifying resin;

about 0–40% of a plasticizer;

about 0.1–2% of an antioxidant; and about 0.1–30% of a surfactant having an HLB of less than 15, said surfactant consisting of a fatty acid ester, the components totaling 100% by weight, and with the proviso that the composition is substantially free of a filler, and wherein the adhesive has a contact angle of less than about 75°.

2. The composition of claim 1 wherein the adhesive has a contact angle of less than about 50°.

3. The composition of claim 1 wherein the plasticizer is mineral oil.

4. The composition of claim 1 wherein the antioxidant is a hindered phenol.

5. The composition of claim 1 wherein the tackifying resin is selected from aliphatic hydrocarbon resins, hydrogenated aromatic hydrocarbon resins, hydrogenated aliphatic hydrocarbon resins or rosin esters.

6. A hydrophilic hot melt adhesive composition, comprising the following components:

about 18–25% of a thermoplastic polymer selected from the group consisting of polybutylenes, S-I-S and S-B-S styrenic block copolymers, and atactic polyalphaolefins;

about 50–60% of a tackifying resin;
about 12–25% of a plasticizer;
about 1% of an antioxidant; and
about 2–15% of a surfactant having an HLB of less than 15; said surfactant consisting of a fatty acid ester, the components totaling 100% by weight, and with the proviso that the composition is substantially free of a filler, and wherein the adhesive has a contact angle of less than about 50°.

7. The composition of claim 6 wherein the plasticizer is mineral oil.

8. The composition of claim 6 wherein the antioxidant is a hindered phenol.

9. The composition of claim 6 wherein the tackifying resin is selected from aliphatic hydrocarbon resins, hydrogenated aromatic hydrocarbon resins, hydrogenated aliphatic hydrocarbon resins or rosin esters.

* * * * *